United States Patent
Funke et al.

(10) Patent No.: US 10,435,352 B2
(45) Date of Patent: Oct. 8, 2019

(54) METHOD FOR SYNTHESIZING 2-ALKYL-4-TRIFLUOROMETHYL-3-ALKYLSULFONYLBENZOIC ACIDS

(71) Applicant: Bayer CropScience Aktiengesellschaft, Monheim am Rhein (DE)

(72) Inventors: Christian Funke, Leichlingen (DE); Thomas Himmler, Odenthal (DE); Sergii Pazenok, Solingen (DE); Christoph Schotes, Düsseldorf (DE); Matthias Beller, Nienhagen (DE); Thomas Schareina, Cammin (DE); Alexander Zapf, Rostock (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/769,765

(22) PCT Filed: Oct. 21, 2016

(86) PCT No.: PCT/EP2016/075361
§ 371 (c)(1),
(2) Date: Apr. 20, 2018

(87) PCT Pub. No.: WO2017/072038
PCT Pub. Date: May 4, 2017

(65) Prior Publication Data
US 2018/0305302 A1  Oct. 25, 2018

(30) Foreign Application Priority Data

Oct. 26, 2015 (EP) .................... 15191494

(51) Int. Cl.
| | |
|---|---|
| *C07C 253/14* | (2006.01) |
| *C07C 255/50* | (2006.01) |
| *C07C 315/02* | (2006.01) |
| *C07C 319/14* | (2006.01) |
| *C07C 319/20* | (2006.01) |
| *C07C 323/62* | (2006.01) |
| *C07C 25/13* | (2006.01) |
| *C07C 323/36* | (2006.01) |

(52) U.S. Cl.
CPC ............ *C07C 253/14* (2013.01); *C07C 25/13* (2013.01); *C07C 255/50* (2013.01); *C07C 315/02* (2013.01); *C07C 319/14* (2013.01); *C07C 319/20* (2013.01); *C07C 323/36* (2013.01); *C07C 323/62* (2013.01)

(58) Field of Classification Search
CPC .................................................. C07C 253/14
See application file for complete search history.

(56) References Cited

U.S. PATENT DOCUMENTS

| | | | |
|---|---|---|---|
| 7,932,211 | B2 | 4/2011 | Ahrens et al. |
| 9,101,141 | B2 | 8/2015 | Koehn et al. |
| 2009/0069184 | A1 | 3/2009 | Ahrens et al. |
| 2014/0080705 | A1 | 3/2014 | Koehn et al. |

FOREIGN PATENT DOCUMENTS

| | | |
|---|---|---|
| CN | 102010351 A | 4/2011 |
| GB | 2194235 A | 3/1988 |
| WO | 2005044007 A1 | 5/2005 |
| WO | 2008125214 A1 | 10/2008 |
| WO | 2012/126932 A1 | 9/2012 |

OTHER PUBLICATIONS

PCT International Search Report for PCT/EP2016/075361, dated Jan. 4, 2017.
Cassar, L., "A new nickel-catalyzed synthesis of aromatic nitriles," Journal of Organometallic chemistry, (1973), vol. 54: C57-C58.
Sakakibara, et al. "The Cyanation of Aromatic Halides Catalyzed by Nickel(0) Complexes Generated In Situ I. General Scope and Limitations," Bull. Chem. Soc. Jpn., (1988), vol. 61: 1985-1990.

*Primary Examiner* — Shawquia Jackson
(74) *Attorney, Agent, or Firm* — McBee Moore Woodward & Vanik IP, LLC

(57) ABSTRACT

A process for preparing 2-alkyl-4-trifluoromethyl-3-alkylsulfonylbenzoic acids of the formula (I) is described.

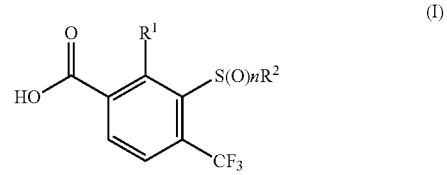

Here, the substituents are radicals such as alkyl and substituted phenyl.

20 Claims, No Drawings

METHOD FOR SYNTHESIZING 2-ALKYL-4-TRIFLUOROMETHYL-3-ALKYLSULFONYLBENZOIC ACIDS

CROSS-REFERENCE TO RELATED APPLICATIONS

This application is a National Stage entry of International Application No. PCT/EP2016/075361, filed Oct. 21, 2016, which claims priority to European Patent Application No. 15191494.2, filed Oct. 26, 2015.

BACKGROUND

Field

The invention relates to a process for preparing 2-alkyl-4-trifluoromethyl-3-alkylsulfonylbenzoic acids which are useful as intermediates for the preparation of agrochemically active compounds.

Description of Related Art

Agrochemically active compounds for the preparation of which 2-alkyl-4-trifluoromethyl-3-alkylsulfonylbenzoic acids are required are known from a number of documents. Thus, herbicidally active 4-(4-trifluoromethyl-3-thiobenzoyl)pyrazoles are known from WO 2008/125214 A1. Herbicidally active N-(1,3,4-oxadiazol-2-yl)arylcarboxamides, including ones having a substitution pattern in the phenyl ring similar to that in the compounds disclosed in WO 2008/125214 A1, are known from WO 2012/126932 A1.

WO 2008/125214 A1 also discloses a process for preparing the compound 2-methyl-4-trifluoromethyl-3-methylsulfonylbenzoic acid. In this process, 3-fluoro-2-methyl-4-trifluoromethylbenzoic acid is reacted with sodium hydride and sodium thiomethylate to form 2-methyl-3-methylthio-4-trifluoromethylbenzoic acid which is subsequently oxidized to 2-methyl-3-methylsulfonyl-4-trifluoromethylbenzoic acid.

Disadvantages of this process are the use of 3-fluoro-2-methyl-4-trifluoromethylbenzoic acid, which owing to the fluorine substituent on the phenyl ring has to be prepared in a complicated manner, and the introduction of the methyl group by metallation of 3-fluoro-2-methyl-4-trifluoromethylbenzoic acid by means of at least 2 molar equivalents of butyllithium at low temperature, followed by reaction with the toxic methyl iodide. This process is complicated and in addition uneconomical because of the only low yield in the introduction of the methyl group (50.7% of theory).

Processes for preparing substituted benzoic acids by means of transition metal-catalyzed cyanations of chloroaromatics and subsequent hydrolysis of the cyano group to the acid group are likewise known. Palladium and nickel compounds, in particular, are frequently used as catalysts, with nickel catalysts being preferred from an economic point of view because of the significantly lower price. The nickel-catalyzed cyanation of aryl halides by means of sodium cyanide in the presence of Ni(PPh$_3$)$_3$ or [aryl-Ni(PPh$_3$)$_2$Cl] is known, J. Organomet. Chem., 54, 1973, C57. The cyanation of trifluoromethyl-substituted haloaromatics is likewise known. Thus, for example, Bull. Chem. Soc. Jpn. 61 (1988) 1985-1990 describes the reaction of meta- or para-chlorobenzotrifluoride by means of potassium cyanide in the presence of NiBr$_2$(PPh$_3$)$_2$ and metallic zinc to form meta- or para-trifluoromethylbenzonitrile. As further ligands, triphenylphosphine (PPh$_3$) and also tri(o-tolyl)phosphine, 1,2-bis(diphenylphosphino)ethane (dppe) and 1,1'-bis(diphenylphosphino)ferrocene (dppf) were used here, with only dppf and PPh$_3$ being found to be effective. CN 102010351 describes a method of preparing 2-fluoro-4-cyanotrifluoromethylbenzene by cyanation of 2,4-dichlorobenzotrifluoride by means of sodium cyanide or potassium cyanide in the presence of NiBr$_2$(PPh$_3$)$_2$. However, the disclosure in the abovementioned documents indicates that the catalytic cyanation of aryl halides often proceeds with unsatisfactory yields.

SUMMARY

It is an object of the present invention to provide a process for preparing 2-alkyl-4-trifluoromethyl-3-alkylsulfonylbenzoic acids, which process overcomes the disadvantages of the processes known from the prior art.

It has now been found that 2-alkyl-4-trifluoromethyl-3-alkylsulfonylbenzoic acids can be prepared inexpensively and in high yields by cyanation of 1,3-dichloro-2-alkyl-4-trifluoromethylbenzenes in the presence of a nickel compound, a phosphine ligand and a further metal, thiolation of the benzonitrile obtained, hydrolysis of the nitrile group and subsequent oxidation of the thio group.

The present invention accordingly provides a process for preparing 2-alkyl-4-trifluoromethyl-3-alkylsulfonylbenzoic acids of the general formula (I), wherein
a) in a first step, a 1,3-dichloro-2-alkyl-4-trifluoromethylbenzene is reacted with a cyanide source in the presence of a nickel compound, a phosphine ligand and a further metal to form a benzonitrile,
b) in a second step, the benzonitrile is reacted with a thiolate in the presence of a phase transfer catalyst to form the corresponding thioether,
c) in a third step, the nitrile group is hydrolyzed to a carboxyl group,
d) in a fourth step, the thio group is oxidized by means of hydrogen peroxide, optionally in the presence of an oxidation catalyst,

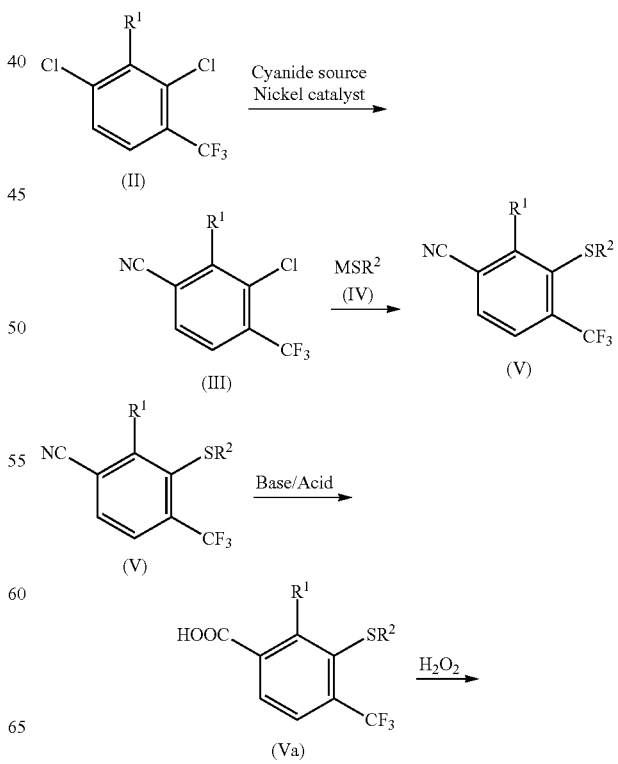

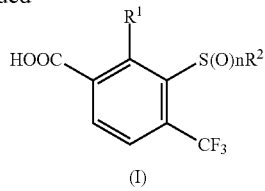

and
e) where the substituents are defined as follows:
   $R^1$ and $R^2$ are each, independently of one another, $C_1$-$C_4$-alkyl or phenyl substituted by s radicals from the group consisting of chloro, fluoro, methoxy and ethoxy,
   M is lithium, sodium or potassium,
   n is 1 or 2,
   s is 1, 2 or 3.

DETAILED DESCRIPTION OF A PREFERRED EMBODIMENT

The compounds of the formula (II) required for carrying out the process of the invention can be obtained by methods which are generally known to those skilled in the art. Thus, for example, WO 2005/044007 A1 describes the preparation of analogous compounds of the formula (II) in which $R^1$ is optionally substituted phenyl. Compounds of the formula (II) in which $R^1$ is $C_1$-$C_4$-alkyl can, for example, be prepared by deprotonation of 2,4-dichlorobenzotrifluoride by means of lithium diisopropylamide and subsequent alkylation using a dialkyl sulfate. GB 2 194 235 A describes a process for preparing 2,6-dichloro-3-trifluoromethyltoluenes.

Significant advantages of the process of the invention are the high yields, the use of inexpensive reagents and the small amounts of waste materials.

In the formulae (I), (II), (III), (IV) and (V), alkyl radicals having more than two carbon atoms can be linear or branched. Alkyl radicals are, for example, methyl, ethyl, n- or i-propyl, n-, i-, t- or 2-butyl.

In the process of the invention, $R^1$ and $R^2$ are each methyl.

In the first step of the process of the invention, inorganic cyanides such as lithium cyanide, sodium cyanide, potassium cyanide, magnesium cyanide, calcium cyanide, zinc cyanide or potassium hexacyanoferrate(II) and organic cyano compounds such as cyanohydrins can be used as cyanide sources. Preference is given to sodium cyanide, potassium cyanide, zinc cyanide, potassium hexacyanoferrate(II) and acetone cyanohydrin. Particular preference is given to sodium cyanide and potassium cyanide. The cyanide sources can be added as pure material either all at once or a little at a time. It is also possible, optionally, to introduce a solution of the cyanide source, for example as a 30% strength solution of sodium cyanide in water. Preference is given to reactions in which from 1 to 10 mol percent of water based on the compound of the formula (II) is present in the reaction mixture. Particular preference is given to from 1.5 to 5 mol percent.

The cyanide source is used in a molar ratio of from 0.7:1 to 2:1, based on the compound of the general formula (II). It is preferably used in an amount of from 1.5:1 to 1:1, particularly preferably from 1.2:1 to 1.1:1.

The reaction in the first step of the process of the invention is generally carried out in a solvent. Preference is given to acetonitrile, acetone, methyl ethyl ketone, tetrahydrofuran (THF), butyronitrile and isopropanol. Particular preference is given to acetonitrile, acetone, THF and methyl ethyl ketone.

In the first step of the process of the invention, it is possible to use nickel(0) and nickel(II) compounds such as bis(1,5-cyclooctadiene)nickel(0), bis(cyclopentadienyl) nickel, methallylnickel chloride dimer, nickel(II) chloride, nickel(II) bromide, nickel(II) acetate, nickel(II) acetylacetonate, nickel(II) nitrate as nickel compound in combination with a phosphine ligand. Preference is given to nickel(II) chloride and nickel(II) bromide, with particular preference being given to nickel(II) bromide. The catalytically active nickel compounds are used in amounts of from 0.1 to 20 mol percent, based on the compound of the general formula (II). Preference is given to from 0.5 to 5 mol percent, particularly preferably from 1 to 2 mol percent.

In the first step of the process of the invention, the following can be used as phosphine ligands: 1,1'-bis(diphenylphosphino)ferrocene (dppf), rac-2,2'-bis(diphenylphosphino)-1,1'-binaphthyl (BINAP), (R)-(+)-2,2'-bis(diphenylphosphino)-1,1'-binaphthyl, (S)-(−)-2,2'-bis(diphenylphosphino)-1,1'-binaphthyl, rac-5,5'-bis(diphenylphosphino)-4,4'-bi-1,3-benzodioxol, 2,2'-bis(diphenylphosphino)-1,1'-biphenyl, rac-2,2'-bis(diphenylphosphino)-5,5',6,6',7,7',8,8'-octahydro-1,1'-binaphthyl, rac-6,6'-bis(diphenylphosphino)-2,2',3,3'-tetrahydro-5,5'-bi-1,4-benzodioxin, rac-2,2'-bis(di-p-tolylphosphino)-1,1'-binaphthyl, bis(2-diphenylphosphinophenyl) ether (dpephos), triphenylphosphine, trifurfurylphosphine, tri(o-tolyl)phosphine, tri(p-tolyl)phosphine, P(tBu$_3$), Cataxcium A. Preference is given to using 1,1'-bis(diphenylphosphino)ferrocene (dppf), rac-2,2'-bis(diphenylphosphino)-1,1'-binaphthyl (BINAP), (R)-(+)-2,2'-bis(diphenylphosphino)-1,1'-binaphthyl, (S)-(−)-2,2'-bis(diphenylphosphino)-1,1'-binaphthyl and bis(2-diphenylphosphinophenyl) ether (dpephos); particular preference is given to 1,1'-bis(diphenylphosphino)ferrocene (dppf), rac-2,2'-bis(diphenylphosphino)-1,1'-binaphthyl (BINAP) and bis(2-diphenylphosphinophenyl) ether (dpephos). Very particular preference is given to bis(2-diphenylphosphinophenyl) ether (dpephos).

The phosphine ligands are used in a molar ratio of from 1:1 to 5:1, based on the nickel compound. They are preferably used in a molar ratio of from 1.5:1 to 3:1, particularly preferably 2:1.

The nickel(II) complex is activated by reduction by addition of a metal such as zinc, magnesium or manganese, preferably zinc. The amount of metal based on the compound of the formula (II) is from 1 to 20 mol percent. Preference is given to using from 2 to 10 mol percent, particularly preferably 6 mol percent. The metal is used in powder form or in the form of fine turnings. The nickel(II) salt used forms the actual active catalyst with the phosphine ligand after reduction. The catalysts can be prepared separately or be formed in situ. Should the activity of the catalyst decrease too greatly during the course of the reaction, it can be increased again by addition of further reducing agent (1-5 mol percent).

The reaction in the first step of the process of the invention is generally carried out at a temperature of from 25 to 100° C., preferably from 60 to 90° C., particularly preferably from 70 to 90° C. The reaction can also be carried out under superatmospheric pressure or reduced pressure.

In the second step of the process of the invention, the compound of the general formula (IV) is used in a ratio of from 1:1 to 2:1 molar equivalents based on the compound of the general formula (III). Preference is given to using from 1.1:1 to 1.5:1, particularly preferably 1.3:1.

The compounds of the general formula (IV) can be prepared either in-situ or ex-situ from the corresponding thiols and a base such as alkali metal hydroxides, alkaline earth metal hydroxides, alkali metal carbonates, alkali metal acetates, alkali metal alkoxides an organic bases. Suitable bases are LiOH, NaOH, KOH, Ca(OH)$_2$, Na$_2$CO$_3$, K$_2$CO$_3$, Cs$_2$CO$_3$, NaOAc, KOAc, LiOAc, NaOMe, NaOEt, NaO-t-Bu, KO-t-Bu, trialkylamines, alkylpyridines, phosphazenes and 1,8-diazabicyclo[5.4.0]undecene.

The reaction of the second step of the process of the invention can also be carried out in a solvent. Preference is given to methyl t-butyl ether, toluene, chlorobenzene, o-dichlorobenzene and water.

As phase transfer catalyst (PTC), use is made of ammonium or phosphonium salts such as tetrahexylammonium chloride, tetrahexylammonium bromide, tetrahexylammonium iodide, tetraoctylammonium chloride, tetraoctylammonium bromide, tetraoctylammonium iodide, Aliquat HTA-1®, Aliquat 134®, dimethyldidecylammonium chloride, dimethyldodecylbenzylammonium chloride, tributylhexadecylammonium chloride, tributylhexadecylammonium bromide, tributyltetradecylphosphonium chloride and tributyltetradecylphosphonium bromide.

Preference is given to Aliquat 134® and tributyltetradecylphosphonium chloride. The phase transfer catalyst is usually employed in an amount of from 0.1 to 10 mol percent, based on the compound of the general formula (III). Preference is given to from 1 to 6 mol percent, particularly preferably from 2 to 4 mol percent.

The reaction in the second step of the process of the invention is generally carried out at a temperature of from 10 to 70° C., preferably from 50 to 60° C.

The hydrolysis of the nitrile group to form a carboxyl group in the third step of the process of the invention is carried out under acidic conditions in the presence of mineral acids such as H$_2$SO$_4$, HCl, HSO$_3$Cl, HF, HBr, HI, H$_3$PO$_4$ or organic acids such as CF$_3$COOH, p-toluenesulfonic acid, methanesulfonic acid or trifluoromethanesulfonic acid, or preferably under basic conditions in the presence of organic bases such as LiOH, NaOH, KOH, Ca(OH)$_2$, Na$_2$CO$_3$, K$_2$CO$_3$, Cs$_2$C03, NaOMe, NaOEt, NaO-t-Bu, KO-t-Bu or organic bases such as trialkylamines, alkylpyridines, phosphazenes and 1,8-diazabicyclo[5.4.0]undecene (DBU). Preference is given to inorganic bases such as NaOH, KOH, Na$_2$CO$_3$, K$_2$CO$_3$.

The reaction in the third step of the process of the invention is generally carried out at a temperature of from 20 to 200° C., preferably from 70 to 150° C., particularly preferably from 110 to 130° C.

The reaction of the third step of the process of the invention is generally carried out in a solvent. Suitable solvents are water, alcohols such as methanol, ethanol, isopropanol or butanol and also aliphatic and aromatic hydrocarbons such as n-hexane, benzene or toluene, which can be substituted by heteroatoms such as fluorine or chlorine, e.g. dichloromethane, dichloroethane, chlorobenzene or dichlorobenzene. Further possibilities are ethers such as diphenyl ether, methyl tert-butyl ether, isopropyl ethyl ether, dioxane, diglyme, dimethyl glycol, dimethoxyethane and THF; amides such as dimethylformamide and N-methyl-2-pyrrolidone (NMP) and mixtures of such solvents. Preference is given to water and alcohols such as methanol, ethanol, isopropanol and butanol. Particular preference is given to methanol and n-butanol.

In the fourth step of the process of the invention, the thio group of the compound (Va) is oxidized by means of hydrogen peroxide, optionally in the presence of an oxidation catalyst. Suitable oxidation catalysts are Na$_2$WO$_4$, Na$_2$MoO$_4$ and hydrates thereof and also sulfuric acid in combination with an organic acid such as acetic acid, formic acid or trifluoroacetic acid.

The oxidation catalysts are used in amounts of from 1 to 20 mol percent, based on the compound of the general formula (Va). Preference is given to from 5 to 15 mol percent, particularly preferably 10 mol percent.

Hydrogen peroxide is used in an amount of from 2 to 10 molar equivalents, preferably from 3 to 8 molar equivalents, particularly preferably from 3.5 to 5 molar equivalents, based on the compound of the general formula (Va). The hydrogen peroxide is usually employed as a 20-35% strength aqueous solution.

The reaction in the fourth step of the process of the invention is generally carried out at a temperature of from 30 to 100° C., preferably from 40 to 95° C., particularly preferably from 70 to 95° C.

The reaction of the fourth step of the process of the invention is generally carried out in a solvent. Suitable solvents are toluene, chlorobenzene, dichlorobenzene, ethyl acetate, butyl acetate, acetic acid, formic acid, water and also mixtures of acetic acid or formic acid with water. Preference is given to toluene, ethyl acetate, butyl acetate, acetic acid, formic acid, water and also mixtures of acetic acid or formic acid with water. Particular preference is given to toluene, butyl acetate, water, and also mixtures of acetic acid or formic acid with water.

The compounds of the formula (II) in which R$^1$ represents particular substituents are novel and are very suitable as starting materials for the first step of the process of the invention. The present invention accordingly also provides the compounds of the formula (IIa)

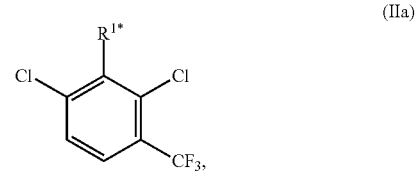

(IIa)

where
R$^{1*}$ is C$_2$-C$_4$-alkyl or phenyl substituted by s radicals from the group consisting of chloro, fluoro, methoxy and ethoxy,
s is 1, 2 or 3.

Compounds of the formula (IIa) in which R$^{1*}$ is ethyl, n-propyl or phenyl are preferred.

Compounds of the formula (III) in which R$^1$ represents particular substituents are novel and are very suitable as starting material for the second step of the process of the invention. The present invention also provides compounds of the formula (IIIa)

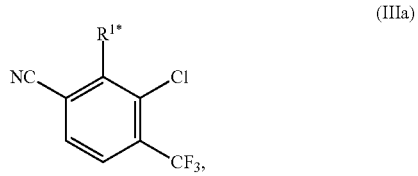

(IIIa)

where
R¹* is $C_1$-$C_4$-alkyl or phenyl substituted by s radicals from the group consisting of chloro, fluoro, methoxy and ethoxy,
s is 1, 2 or 3.

R¹* in formula (IIIa) is preferably methyl, ethyl, n-propyl, isopropyl, n-butyl or phenyl.

R¹* in formula (IIIa) is particularly preferably methyl, ethyl, n-propyl or phenyl. R¹* in formula (IIIa) is very particularly preferably methyl.

Compounds of the formula (V) are novel and are very suitable as starting material for the third step of the process of the invention. The present invention accordingly also provides compounds of the formula (V),

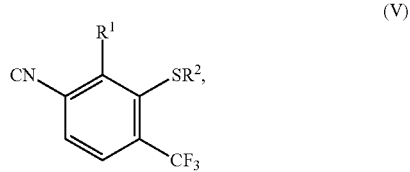

(V)

where
$R^1$ and $R^2$ are each, independently of one another, $C_1$-$C_4$-alkyl or phenyl substituted by s radicals from the group consisting of chloro, fluoro, methoxy and ethoxy,
s is 1, 2 or 3.

Preference is given to $R^1$ and $R^2$ in formula (V) each being, independently of one another, methyl, ethyl, n-propyl, isopropyl or n-butyl. Particular preference is given to $R^1$ being methyl and $R^2$ being methyl or ethyl.

The following examples illustrate the invention.

Preparation of 2-methyl-3-(methylsulfonyl)-4-(trifluoromethyl)benzoic Acid

Step 1: 3-Chloro-2-methyl-4-(trifluoromethyl)benzonitrile (Variant 1)

Under an argon atmosphere, 0.44 g of $NiBr_2$ (2 mmol, 2 mol %) and 2.15 g of DPEPhos (4 mmol, 4 mol %) together with 0.39 g of zinc powder (6 mmol, 6 mol %) are placed in a reaction vessel. 200 ml of acetonitrile are added and the internal temperature is increased to 50° C. while stirring. After 44 minutes, the internal temperature is reduced to 10° C. After 48 minutes at this temperature, 2,4-dichloro-3-methyltrifluoromethylbenzene was added (22.9 g, 100 mmol, 1 equivalent), followed by sodium cyanide (5.4 g, 110 mmol, 1.1 equivalent). The internal temperature is increased to 80° C. and the reaction mixture is stirred vigorously for 18 hours. After cooling, the reaction mixture is evaporated under reduced pressure and subsequently admixed with heptane and greatly diluted NaOH. The two-phase mixture is filtered, the organic phase is separated off and the aqueous phase is washed once with heptane. The combined organic phases are washed once with water and subsequently evaporated completely under reduced pressure. This gives 3-chloro-2-methyl-4-(trifluoromethyl)benzonitrile in a yield of 90%.

GC/MS: m/e=219.1 (M); 199.1 (M-HF); 184.1 (M-Cl).

Step 1: 3-Chloro-2-methyl-4-(trifluoromethyl)benzonitrile (Variant 2)

Under an argon atmosphere, 2.96 g of $NiBr_2$-DPEPhos complex (3.9 mmol, 1 mol %) and 2.11 g of DPEPhos (3.0 mmol, 1 mol %) together with 1.04 g of zinc powder (15.7 mmol, 4 mol %) are placed in a reaction vessel. 400 ml of acetonitrile are added and the internal temperature is increased to 50° C. while stirring. After 20 minutes, the internal temperature is reduced to 25° C. and 2,4-dichloro-3-methyltrifluoromethylbenzene (91.6 g, 391.6 mmol, 1 equivalent) followed by sodium cyanide (23.03 g, 469.9 mmol, 1.2 equivalents), zinc (0.53 g, 7.8 mmol, 2 mol %) and water (0.16 ml, 8.9 mmol, 2.3 mol %) are added. The internal temperature is increased to 80° C. and the reaction mixture is stirred vigorously for 7 hours. Zinc is then again added (0.53 g, 7.8 mmol, 2 mol %) and the mixture is stirred vigorously for a further 13 hours. After cooling, the reaction mixture is evaporated under reduced pressure and subsequently admixed with methylcyclohexane and greatly diluted NaOH. The two-phase mixture is filtered and the organic phase is separated off. The latter is washed with water, dried over sodium sulfate and subsequently evaporated completely under reduced pressure. This gives 3-chloro-2-methyl-4-(trifluoromethyl)benzonitrile in a yield of 89%.

Step 2: 2-Methyl-3-(methylsulfanyl)-4-(trifluoromethyl)benzonitrile 21.4 g of 3-chloro-2-methyl-4-(trifluoromethyl)benzonitrile (88.7 mmol, 1 equivalent) are placed in a reaction vessel at 50° C. A 21% strength solution of NaSMe in $H_2O$ (38.5 ml, 115.4 mmol, 1.3 equivalents) is added, followed by tributyltetradecylphosphonium chloride (773 mg, 1.78 mmol, 2 mol %). The mixture is stirred at from 50 to 53° C. for 16.5 hours, after which monitoring of the reaction by GC indicates complete conversion into the target product. The mixture is cooled and admixed with a mixture of MTBE and water. The phases are separated, the organic phase is washed twice with water and once with saturated aqueous sodium chloride solution. The organic phase is then evaporated completely under reduced pressure. This gives 23.7 g of 2-methyl-3-(methylsulfanyl)-4-(trifluoromethyl)benzonitrile (purity according to quant. NMR: 88%, quantitative yield).

Step 3: 2-Methyl-3-(methylsulfanyl)-4-(trifluoromethyl)benzoic Acid 12.75 g (318.8 mmol, 3.5 equivalents) of solid NaOH, 12.75 ml of water and 105 ml of n-butanol are added to 23.4 g of 2-methyl-3-(methylsulfanyl)-4-(trifluoromethyl)benzonitrile (purity: 90%, 91 mmol, 1 equivalent). The mixture is heated in an oil bath having a bath temperature of 125° C. for 5 hours, after which monitoring of the reaction by RP-HPLC indicates complete conversion. The mixture is cooled to room temperature, and mixed with water and the solvent mixture is removed under reduced pressure. The mixture is diluted again with water and evaporated in order to remove the n-butanol as completely as possible. A little water is subsequently added and the mixture is acidified with concentrated aqueous HCl while cooling. The resulting greasy solid becomes more solid over time while stirring. The mixture is cooled in an ice bath, filtered and washed with cold water. The filter cake is washed twice with 50 ml of heptane and subsequently dried. This gives 23.1 g of 2-methyl-3-(methylsulfanyl)-4-(trifluoromethyl)benzoic acid (purity according to quant. NMR: 89%, 90% yield) as a white solid.

Step 4: 2-Methyl-3-(methylsulfonyl)-4-(trifluoromethyl)benzoic Acid (Variant 1)

2-Methyl-3-(methylsulfanyl)-4-(trifluoromethyl)benzoic acid (9.6 g, 38 mmol, 1 equivalent) is dissolved in 60 ml of n-butyl acetate and 1.1 g (3.8 mmol, 0.1 equivalent) of sodium tungstate dihydrate are added. The mixture is intensively stirred and heated to 55° C. 16.2 ml (190 mmol, 5 equivalents) of 35% strength hydrogen peroxide solution are metered in by syringe pump over a period of 2 hours at an internal temperature of 55-60°. The mixture is stirred further at this temperature for from 8 to 10 hours. The mixture is then cooled and brought to pH=0 by means of dilute HCl. The reaction solution is heated to 60° C. and the phases are separated hot. The major part of the n-butyl acetate is removed under reduced pressure. The thick slurry formed is cooled and admixed with a little toluene. The precipitate is filtered off with suction, washed with water and dried. This gives 8.7 g of 2-methyl-3-(methylsulfonyl)-4-(trifluoromethyl)benzoic acid (81% yield) as a white solid.

Step 4: 2-Methyl-3-(methylsulfonyl)-4-(trifluoromethyl) benzoic Acid (Variant 2)

2-Methyl-3-(methylsulfanyl)-4-(trifluoromethyl)benzoic acid (112.5 g, 450 mmol, 1 equivalent) is suspended in 225 ml of water and 56 ml of acetic acid. 11 g (33.7 mmol) of sodium tungstate dihydrate are then added. The mixture is intensively stirred and heated to 95° C. 194 g (1.575 mol, 3.5 equivalents) of 27.6% strength hydrogen peroxide solution are then metered in by syringe pump over a period of 4 hours at an internal temperature of 95°. The mixture is stirred further at this temperature for 6 hours. The mixture is then cooled to 2° C., the solid is filtered off, washed with water and dried. This gives 120 g of 2-methyl-3-(methylsulfonyl)-4-(trifluoromethyl)benzoic acid (95% yield) as a white solid.

WORKING EXAMPLES OF THE PREPARATION OF COMPOUNDS OF THE FORMULA (II)

Example 1: Preparation of 2,4-dichloro-3-methylbenzotrifluoride

A 1 molar solution of lithium diisopropylamide in THF (0.6 mol) was slowly added dropwise to a solution of 2,4-dichlorobenzotrifluoride (107 g, 0.5 mol) and dimethyl sulfate (75.6 g, 0.6 mol) in 500 ml of THF at −50° C. The mixture was stirred at −50° C. for 2 hours and warmed to 20° C. 200 ml of 1 N HCl as aqueous solution were then slowly added dropwise and the THF was subsequently removed under reduced pressure at 40° C. The product was extracted with 300 ml of hexane, the extract was washed with water and dried over MgSO$_4$. The hexane was removed under a vacuum of 40 mbar. This gave 110 g of a mixture which, according to GC/MS analysis, contained 78% of 2,4-dichloro-3-methylbenzotrifluoride, 10% of 2,4-dichlorobenzotrifluoride (starting material) and 12% of 2,4-dichloro-3-ethylbenzotrifluoride. The desired product can be obtained in pure form by crystallization from methanol at −30° C.

Yield: 73 g (64% of theory). M.p. 30-32° C. B.p. 82-84° C./8 mbar.

Example 2: Preparation of 2,4-dichloro-3-ethylbenzotrifluoride (Variant 1)

2,4-Dichloro-3-ethylbenzotrifluoride

A 1 molar solution of lithium diisopropylamide in THF (1.1 mol) was slowly added dropwise to a solution of 2,4-dichlorobenzotrifluoride (107 g, 0.5 mol) and dimethyl sulfate (138 g, 1.1 mol) in 500 ml of THF at −50° C. The mixture was stirred at −50° C. for 2 hours and warmed to 20° C. 100 ml of 1 N HCl as aqueous solution were then slowly added dropwise and THF was subsequently removed under reduced pressure at 40° C.

The product was extracted with 300 ml of hexane, the extract was washed with water and dried over MgSO$_4$. The solution was concentrated in a vacuum of 40 mbar. This gave 125 g of a mixture which, according to GC/MS analysis, contained 25% of 2,4-dichloro-3-methylbenzotrifluoride, 5% of 2,4-dichlorobenzotrifluoride (starting material) and (70%) of 2,4-dichloro-3-ethylbenzotrifluoride. The desired product can be purified by distillation under reduced pressure using a Vigreux column.

Yield: 69 g (58% of theory). B.p. 114-118° C./15 mbar.

Preparation of 2,4-dichloro-3-methylbenzotrifluoride (Variant 2)

A 1 molar solution of lithium diisopropylamide in THF (0.6 mol) was slowly added dropwise to a solution of 2,4-dichlorobenzotrifluoride (107 g, 0.5 mol) and diethyl sulfate (92.4 g, 0.6 mol) in 500 ml of THF at −50° C. The mixture was stirred at −50° C. for 2 hours and warmed to 20° C. 100 ml of 1 N HCl as aqueous solution were then slowly added dropwise and THF was subsequently removed under reduced pressure at 40° C.

The product was extracted with 300 ml of hexane, the extract was washed with water and dried over MgSO$_4$. The solution was concentrated in a vacuum of 40 mbar. This gave 116 g of a mixture which, according to GC/MS analysis, contained 78% of 2,4-dichloro-3-ethylbenzotrifluoride. The desired product can be purified by distillation under reduced pressure using a Vigreux column.

The invention claimed is:

1. A process for preparing a 2-alkyl-4-trifluoromethyl-3-alkylsulfonylbenzoic acid of formula (I), comprising:

a) reacting a 1,3-dichloro-2-alkyl-4-trifluoromethylbenzene of formula (II) with a cyanide source in the presence of a nickel catalyst, to form a benzonitrile of formula (III), wherein a nickel compound, a phosphine ligand and a further metal are used to form the nickel catalyst, b) reacting the benzonitrile of formula (III) with MSR$^2$ of formula (IV) in the presence of a phase transfer catalyst to form a corresponding thioether of formula (V), c) hydrolyzing the nitrile group of the thioether of formula (V) to a carboxyl group to form a thioether of formula (Va), d) oxidizing the thio group of the thioether of formula (Va), as shown in the below sequence:

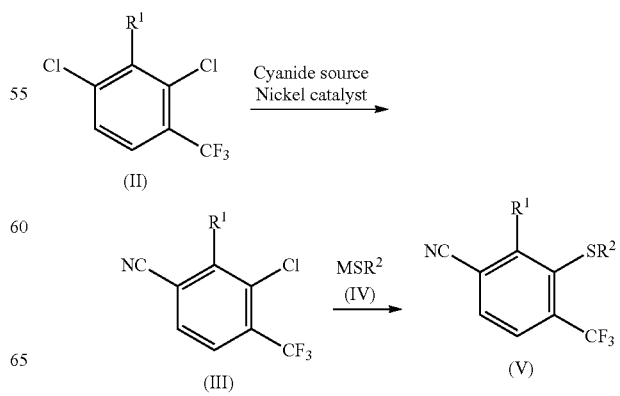

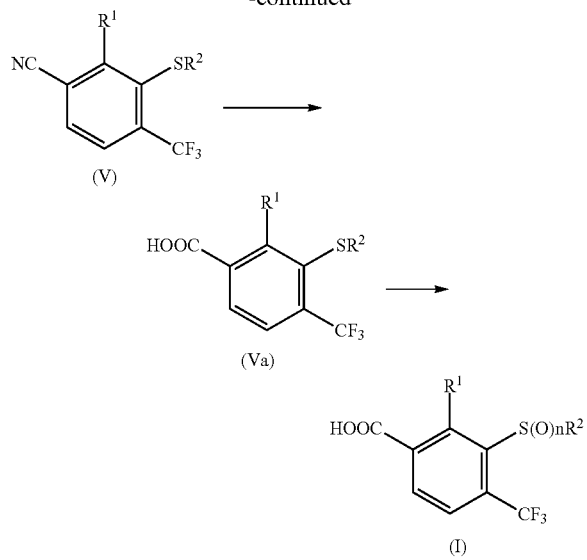

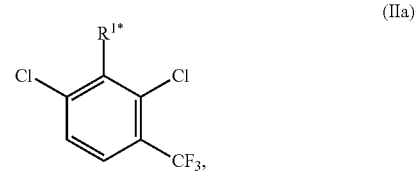

and e) wherein the substituents are defined as follows:
$R^1$ and $R^2$ are each, independently of one another, $C_1$-$C_4$-alkyl or phenyl substituted by s radicals selected from the group consisting of chloro, fluoro, methoxy and ethoxy,
M is lithium, sodium or potassium,
n is 1 or 2,
is 1, 2 or 3.

2. The process as claimed in claim 1, wherein $R^1$ and $R^2$ are each methyl.

3. The process as claimed in claim 1, wherein the cyanide source is sodium cyanide, potassium cyanide, zinc cyanide, potassium hexacyanoferrate(II) or acetone cyanohydrin.

4. The process as claimed in claim 1, wherein the cyanide source is used in a molar ratio of from 1:1 to 1.5:1, based on the 1,3-dichloro-2-alkyl-4-trifluoromethylbenzene of formula (II).

5. The process as claimed in claim 1, wherein the nickel compound is nickel(II) chloride or nickel(II) bromide in an amount of from 0.5 to 5 mol percent and the phosphine ligand is in an amount of from 0.5 to 10 mol percent based on the 1,3-dichloro-2-alkyl-4-trifluoromethylbenzene of formula (II).

6. The process as claimed in claim 1, wherein the phosphine ligand is bis(2-diphenylphosphinophenyl) ether (dpephos), bis(diphenylphosphino)ferrocene (dppf) or rac-2,2'-bis(diphenylphosphino)-1,1'-binaphthyl (BINAP), and wherein the phosphine ligand is in a molar ratio of from 1.5:1 to 3:1, based on the nickel compound.

7. The process as claimed in claim 1, wherein the phosphine ligand is bis(2-diphenylphosphinophenyl) ether (dpephos).

8. The process as claimed in claim 1, wherein the further metal is from 2 to 10 mol percent of zinc, based on the 1,3-dichloro-2-alkyl-4-trifluoromethylbenzene of formula (II).

9. A compound of formula (IIa):

wherein $R^{1*}$ is ethyl, n-propyl or phenyl.

10. The process according to claim 1, wherein d) comprises oxidizing the thio group in the presence of an oxidation catalyst.

11. The process as claimed in claim 10, wherein the oxidation catalyst is $Na_2WO_4$ in an amount of from 5 to 15 mol percent, and hydrogen peroxide is present in an amount of from 3 to 8 molar equivalents, in each case based on the compound of formula (Va).

12. The process according to claim 5, wherein the nickel compound is nickel(II) chloride.

13. The process according to claim 5, wherein the nickel compound is nickel(II) bromide.

14. The process according to claim 1, wherein the phosphine ligand is bis(2-diphenylphosphinophenyl) ether (dpephos) in a molar ratio of from 1.5:1 to 3:1, based on the nickel compound.

15. The process according to claim 1, wherein the phosphine ligand is bis(diphenylphosphino)ferrocene (dppf) in a molar ratio of from 1.5:1 to 3:1, based on the nickel compound.

16. The process according to claim 1, wherein the phoshine ligand is rac-2,2'-bis(diphenylphosphino)-1,1'-binaphthyl (BINAP) in a molar ratio of from 1.5:1 to 3:1, based on the nickel compound.

17. The process according to claim 3, wherein the cyanaide source is sodium cyanide, or potassium cyanide.

18. The process according to claim 1, wherein in (c), said hydrolyzing is performed with a base or acid.

19. The process according to claim 1, wherein in (d), said oxidizing is performed with hydrogen peroxide.

20. The process according to claim 2, wherein M is sodium.

* * * * *